United States Patent
Wang et al.

(10) Patent No.: US 9,305,039 B2
(45) Date of Patent: *Apr. 5, 2016

(54) INDEXING OF LARGE SCALE PATIENT SET

(71) Applicant: INTERNATIONAL BUSINESS MACHINES CORPORATION, Armonk, NY (US)

(72) Inventors: Fei Wang, Yorktown Heights, NY (US); Jun Wang, White Plains, NY (US)

(73) Assignee: International Business Machines Corporation, Armonk, NY (US)

( * ) Notice: Subject to any disclaimer, the term of this patent is extended or adjusted under 35 U.S.C. 154(b) by 150 days.

This patent is subject to a terminal disclaimer.

(21) Appl. No.: 13/967,062

(22) Filed: Aug. 14, 2013

(65) Prior Publication Data
US 2014/0172870 A1   Jun. 19, 2014

Related U.S. Application Data

(63) Continuation of application No. 13/719,427, filed on Dec. 19, 2012.

(51) Int. Cl.
*G06F 17/30* (2006.01)
*G06F 19/00* (2011.01)

(52) U.S. Cl.
CPC ...... *G06F 17/30321* (2013.01); *G06F 19/3443* (2013.01); *G06F 17/30613* (2013.01); *G06F 17/30619* (2013.01)

(58) Field of Classification Search
CPC ................ G06F 17/30321; G06F 17/30613
USPC ........................................... 707/741
See application file for complete search history.

(56) References Cited

U.S. PATENT DOCUMENTS

| 5,781,906 | A * | 7/1998 | Aggarwal | G06F 17/30327 |
| 5,938,594 | A * | 8/1999 | Poon | G06F 17/18 600/300 |
| 6,505,205 | B1 * | 1/2003 | Kothuri | G06F 17/30327 |
| 6,912,549 | B2 * | 6/2005 | Rotter | G06F 19/322 |

(Continued)

FOREIGN PATENT DOCUMENTS

| EP | 1207464 | 5/2002 |
| EP | 2030131 | 3/2009 |

OTHER PUBLICATIONS

Bentley, J., et al. "Multidimensional Binary Search Trees Used for Associative Searching" Communications of the ACM. vol. 18. No. 9. Sep. 1975. pp. 509-517.

(Continued)

*Primary Examiner* — Pierre Vital
*Assistant Examiner* — Nargis Sultana
(74) *Attorney, Agent, or Firm* — Tutunjian & Bitetto, P.C.; Louis J. Percello (57) ABSTRACT

Systems and methods for indexing data include formulating an objective function to index a dataset, a portion of the dataset including supervision information. A data property component of the objective function is determined, which utilizes a property of the dataset to group data of the dataset. A supervised component of the objective function is determined, which utilizes the supervision information to group data of the dataset. The objective function is optimized using a processor based upon the data property component and the supervised component to partition anode into a plurality of child nodes.

17 Claims, 3 Drawing Sheets

(56) References Cited

U.S. PATENT DOCUMENTS

| | | | | |
|---|---|---|---|---|
| 8,676,805 | B1* | 3/2014 | Long | G06N 7/005 707/737 |
| 2002/0022973 | A1* | 2/2002 | Sun | G06Q 10/10 705/3 |
| 2002/0075261 | A1* | 6/2002 | Brokenshire | G06T 17/005 345/420 |
| 2003/0135495 | A1* | 7/2003 | Vagnozzi | G06F 17/30324 |
| 2003/0145014 | A1* | 7/2003 | Minch | G06F 17/30705 |
| 2003/0216939 | A1* | 11/2003 | Bito | G06Q 50/22 705/2 |
| 2004/0015070 | A1* | 1/2004 | Liang | A61B 19/52 600/407 |
| 2004/0019598 | A1* | 1/2004 | Huang | G06K 9/6282 |
| 2004/0098204 | A1* | 5/2004 | Milosavljevic | G01N 35/00871 702/20 |
| 2004/0249831 | A1* | 12/2004 | Fagin | G06F 17/30483 |
| 2007/0142873 | A1* | 6/2007 | Esteller | A61B 5/0482 607/45 |
| 2007/0288417 | A1* | 12/2007 | Aggarwal | G06F 17/3061 706/52 |
| 2008/0114800 | A1* | 5/2008 | Gazen | G06F 17/30861 |
| 2008/0228769 | A1* | 9/2008 | Lita | G06F 19/345 |
| 2008/0301077 | A1* | 12/2008 | Fung | G06F 19/345 706/46 |
| 2010/0094824 | A1* | 4/2010 | Pennington | G06F 17/30321 707/705 |
| 2010/0131434 | A1* | 5/2010 | Magent | G06F 19/322 706/11 |
| 2010/0136553 | A1* | 6/2010 | Black | C12Q 1/6886 435/6.16 |
| 2010/0153375 | A1* | 6/2010 | Bilas | G06F 17/30153 707/723 |
| 2010/0174714 | A1* | 7/2010 | Asmundsson | G06F 17/30327 707/737 |
| 2010/0280350 | A1* | 11/2010 | Zhang | A61B 5/4803 600/407 |
| 2011/0302163 | A1* | 12/2011 | Rhinelander | G06F 17/30598 707/737 |
| 2012/0041277 | A1* | 2/2012 | Ebadollahi | A61B 5/0205 600/301 |
| 2012/0117076 | A1* | 5/2012 | Austermann | G06F 17/30542 707/741 |
| 2012/0130771 | A1* | 5/2012 | Kannan | G06Q 10/06398 705/7.32 |
| 2012/0150498 | A1* | 6/2012 | Shastri | G06F 19/3437 703/2 |
| 2012/0159393 | A1* | 6/2012 | Sethi | G06F 17/30554 715/830 |
| 2012/0209625 | A1* | 8/2012 | Armstrong | G06F 19/326 705/3 |
| 2013/0282721 | A1* | 10/2013 | McCloskey | G06K 9/6281 707/737 |
| 2013/0325759 | A1* | 12/2013 | Rachevsky | G06N 99/005 706/12 |
| 2013/0339060 | A1* | 12/2013 | Delaney | G06Q 10/06 705/3 |
| 2014/0095512 | A1* | 4/2014 | Sun | G06F 17/30 707/747 |
| 2014/0337353 | A1* | 11/2014 | Hickey | G06F 19/3443 707/741 |

OTHER PUBLICATIONS

Gionis, A., et al. "Similarity Search in High Dimensions Via Hashing" Proceedings of 25th International Conference on Very Large Data Bases. Sep. 1999. pp. 518-529.

Gong, Y., et al. "Iterative Quantization: A Procrustean Approach to Learning Binary Codes" 2011 IEEE Conference on Computer Vision and Pattern Recognition. Jun. 2011. pp. 817-824.

Kulis, B., et al. "Learning to Hash With Binary Reconstructive Embeddings" 23rd Annual Conference on Neural Information Processing Systems 2009. Dec. 2009. pp. 1-9.

Liu, T., et al. "An Investigation of Practical Approximate Nearest Neighbor Algorithms" Neural Information Processing Systems, NIPS 2004. Dec. 2004. (8 Pages).

Liu, W., et al. "Supervised Hashing With Kernels" IEEE Conference on Computer Vision and Pattern Recognition. Jun. 2012. pp. 2074-2081.

Ng, A., et al. "On Spectral Clustering: Analysis and an Algorithm" In Advances in Neural Information Processing Systems. 2001. (8 Pages).

Omohundro, S. "Efficient Algorithms With Neural Network Behavior" Complex Systems, vol. 1, No. 2. 1987. pp. 273-347.

Shakhnarovich, G., et al. "Nearest-Neighbor Methods in Learning and Vision: Theory and Practice" Massachusetts Institute of Technology, The MIT Press. 2005. (26 pages).

Sun, J., et al. "Localized Supervised Metric Learning on Temporal Physiological Data" 2010 20th International Conference on Pattern Recognition. Aug. 2010. (4 Pages).

Uhlmann, J. "Satisfying General Proximity/Similarity Queries With Metric Trees" Information Processing Letters, vol. 40, No. 4. Nov. 1991. pp. 175-179.

Wang, F., et al. "Integrating Distance Metrics Learned From Multiple Experts and Its Application in Patient Similarity Assessment" Proceedings of the Eleventh SIAM International Conference on Data Mining. Apr. 2007, pp. 59-70.

Wang, J., et al. "Semi-Supervised Hashing for Large Scale Search" IEEE Transactions on Pattern Analysis and Machine Intelligence, Vol. 6, No. 1. Jan. 2010. pp. 1-14.

Wang, J., et al. "Sequential Projection Learning for Hashing With Compact Codes" Proceedings of the 27th International Conference on Machine Learning. Jun. 2010. (8 Pages).

Wang, F., et al. "Two Heads Better Than One: Metric+Active Learning and Its Applications for It Service Classification" 2009 9th IEEE International Conference on Data Mining. Dec. 2009. pp. 1022-1027.

Weinberger, K., et al. "Unsupervised Learning of Image Manifolds by Semidefinite Programming" Proceedings of the 2004 IEEE Computer Society Conference on Computer Vision and Pattern Recognition. Jun./Jul. 2004. (9 Pages).

Zhang, D., et al. "Composite Hashing With Multiple Information Sources" Proceedings of the 34th International ACM SIGIR Conference on Research and Development in Information Retrieval. Jul. 2011. (10 Pages).

* cited by examiner

Formulate an objective function to index a dataset, a portion of the dataset including supervision information
302

↓

Determine a data property component of the objective function which utilizes a property of the dataset to group data of the dataset
304

- Determine a data property component by maximizing variance of the dataset
  306

- Determine a data property component by equally distributing data clusters around the median of the dataset
  308

↓

Determine a supervised component of the objective function which utilizes the supervision information to group data of the dataset
310

- Determine a supervised component by minimizing pairwise distances of data identified as similar by the supervision information and maximizing pairwise distances of data identified as dissimilar by the supervision information
  312

- Determine a supervised component by applying the dataset as a linear prediction function
  314

↓

Optimize the objective function based upon the data property component and the supervised component to partition a node into a plurality of child nodes
316

- Recursively optimize the objective function at each node to provide a binary space partitioning tree
  318

FIG. 3

INDEXING OF LARGE SCALE PATIENT SET

RELATED APPLICATION INFORMATION

This application is a Continuation application of co-pending U.S. patent application Ser. No. 13/719,427 filed on Dec. 19, 2012, incorporated herein by reference in its entirety.

BACKGROUND

1. Technical Field

The present invention relates to data indexing and retrieval and more particularly to data indexing and retrieval of similar patients from massive patient electronic medical records.

2. Description of the Related Art

With the rapid development of information technologies, a tremendous amount of data has become readily available in various application domains. This big data era presents challenges for many conventional data analytic tools, platforms and systems. In medical research, electronic medical records (EMR) have gained in popularity to include massive amounts of patient medical information. The ability to analyze big data in modern healthcare systems is important in the improvement of the quality of care delivery.

Patient similarity evaluation aims at estimating the clinical affinity and diagnostic proximity of patients. Many medical applications are based upon patient similarity evaluation, such as risk stratification and comparative effectiveness research. However, existing approaches for patient similarity evaluation are inefficient in handling massive amounts of data.

SUMMARY

A method for indexing data includes formulating an objective function to index a dataset, a portion of the dataset including supervision information. A data property component of the objective function is determined, which utilizes a property of the dataset to group data of the dataset. A supervised component of the objective function is determined, which utilizes the supervision information to group data of the dataset. The objective function is optimized using a processor based upon the data property component and the supervised component to partition a node into a plurality of child nodes.

A computer readable storage medium comprises a computer readable program for indexing data. The computer readable program when executed on a computer causes the computer to perform the following steps. An objective function is formulated to index a dataset, a portion of the dataset including supervision information. A data property component of the objective function is determined, which utilizes a property of the dataset to group data of the dataset. A supervised component of the objective function is determined, which utilizes the supervision information to group data of the dataset. The objective function is optimized using a processor based upon the data property component and the supervised component to partition a node into a plurality of child nodes.

A system for indexing data includes a formulation module configured to formulate an objective function to index a dataset stored on a computer readable storage medium, a portion of the dataset including supervision information. A data property module is configured to determine a data property component of the objective function which utilizes a property of the dataset to group data of the dataset. A supervision module is configured to determine a supervised component of the objective function which utilizes the supervision information to group data of the dataset. An optimization module is configured to optimize the objective function based upon the data property component and the supervised component to partition a node into a plurality of child nodes.

These and other features and advantages will become apparent from the following detailed description of illustrative embodiments thereof, which is to be read in connection with the accompanying drawings.

BRIEF DESCRIPTION OF DRAWINGS

The disclosure will provide details in the following description of preferred embodiments with reference to the following figures wherein.

DETAILED DESCRIPTION OF PREFERRED EMBODIMENTS

In accordance with the present principles, systems and methods of data indexing are provided. An objective function is formulated to index a dataset, which may include patient medical information. A portion of the dataset includes supervision information identifying data pairs that are similar and dissimilar. The remaining portion of the dataset does not include supervision information.

The objective function includes a data property component and a supervision component. A tradeoff parameter is also included to balance the contributions from each component. The data property component utilizes a property of the dataset to group patients for all of the dataset (i.e., both supervised and unsupervised). In one embodiment, the data property component is determined by maximizing the variance of the dataset. Maximizing variance may include, e.g., principal component analysis and maximum variance unfolding. In another embodiment, the data property component is determined by separating clusters to form two balanced data clusters around the median of the projected data. The supervision component utilizes the supervision information to group patients using the supervised portion of the dataset. In one embodiment, the supervision component is determined by minimizing the pairwise distances for similar data pairs while maximizing the pairwise distances for dissimilar data pairs. In another embodiment, supervision component is determined by treating the projection of the dataset as a linear prediction function. Other embodiments of the data property component and the supervision component are also contemplated.

The objective is optimized based on the determined data property component and the supervision component to partition a node into a plurality (e.g., 2) of children nodes. The optimization is recursively performed on each node to provide a binary space partitioning tree. Advantageously, the present principles provide for a more robust and accurate indexing tree without a significant increase in search time and tree construction time.

As will be appreciated by one skilled in the art, aspects of the present invention may be embodied as a system, method or computer program product. Accordingly, aspects of the present invention may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, aspects of the present invention may take the form of a computer program product embodied in one or more computer readable medium(s) having computer readable program code embodied thereon.

Any combination of one or more computer readable medium(s) may be utilized. The computer readable medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that can contain, or store a program for use by or in connection with an instruction execution system, apparatus, or device.

A computer readable signal medium may include a propagated data signal with computer readable program code embodied therein, for example, in baseband or as part of a carrier wave. Such a propagated signal may take any of a variety of forms, including, but not limited to, electro-magnetic, optical, or any suitable combination thereof. A computer readable signal medium may be any computer readable medium that is not a computer readable storage medium and that can communicate, propagate, or transport a program for use by or in connection with an instruction execution system, apparatus, or device.

Program code embodied on a computer readable medium may be transmitted using any appropriate medium, including but not limited to wireless, wireline, optical fiber cable, RE, etc., or any suitable combination of the foregoing. Computer program code for carrying out operations for aspects of the present invention may be written in any combination of one or more programming languages, including an object oriented programming language such as Java, Smalltalk, C++ or the like and conventional procedural programming languages, such as the "C" programming language or similar programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Aspects of the present invention are described below with reference to flowchart illustrations and/or block diagrams of methods, apparatus (systems) and computer program products according to embodiments of the invention. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks. The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

The flowchart and block diagrams in the Figures illustrate the architecture, functionality, and operation of possible implementations of systems, methods and computer program products according to various embodiments of the present invention. In this regard, each block in the flowchart or block diagrams may represent a module, segment, or portion of code, which comprises one or more executable instructions for implementing the specified logical function(s). It should also be noted that, in some alternative implementations, the functions noted in the blocks may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

Figure 1:
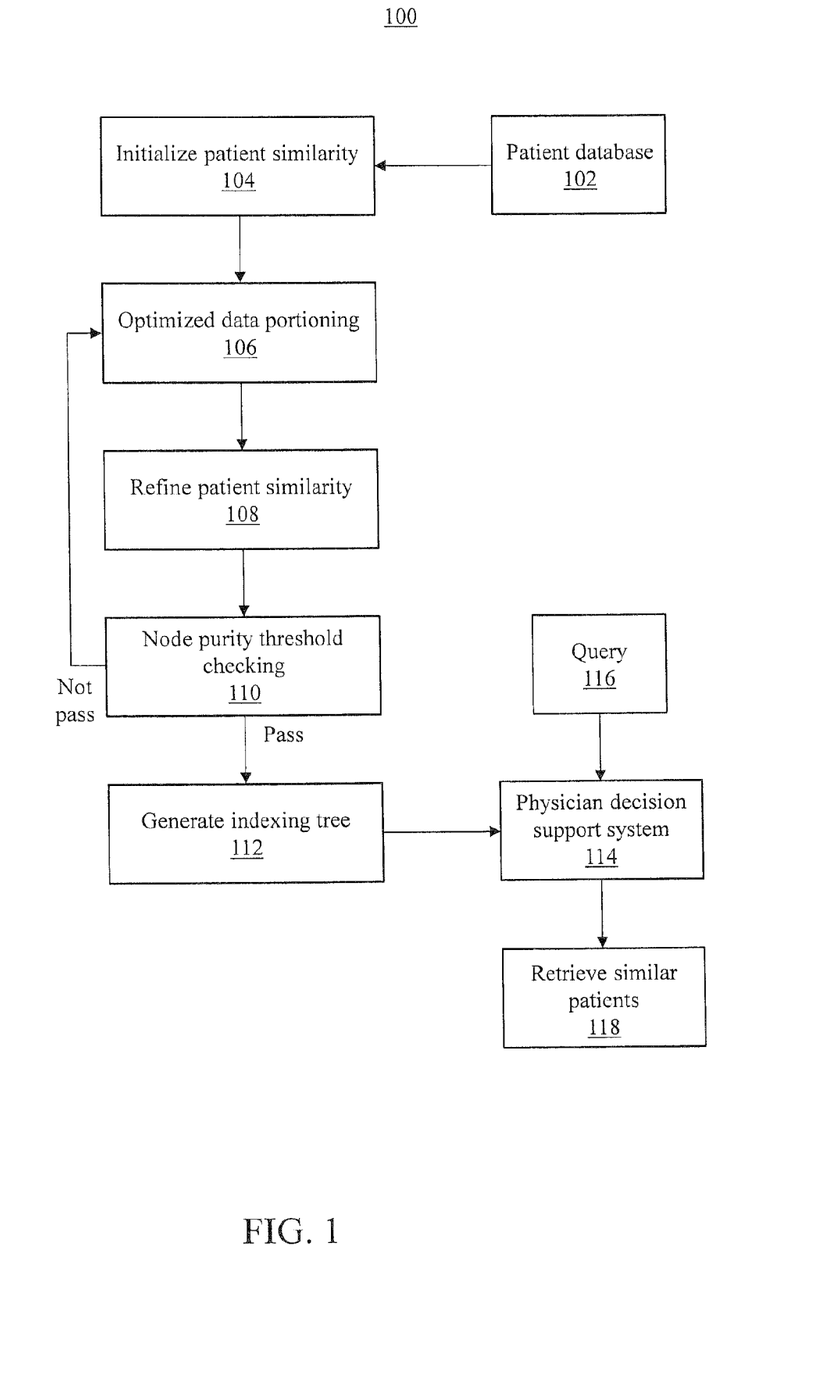
FIG. 1 is a block/flow diagram showing a high level application in accordance with one illustrative embodiment.

Referring now to the drawings in which like numerals represent the same or similar elements and initially to FIG. 1, a block/flow diagram showing a high level diagram 100 of an application of the present principles is illustratively depicted in accordance with one embodiment. The diagram 100 shows an exemplary application of the present principles in a physician decision support system to identify similar patients from a query patient. It should be understood that the present principles are not limited to patient similarity applications or medical applications. Other applications are also contemplated within the scope of the present principles.

A patient database 102 is used to initialize a patient similarity 104. Patient database may include, e.g., Electronic Medical Records (EMR), which may be big data. An initial patient similarity is deployed to evaluate similar patients based on unprocessed data of the patient database 102. An optimized data partitioning 106 is then performed in accordance with the present principles. Advantageously, the inventive optimized data partitioning provides a semi-supervised framework to learn each data partition, which leverages both expert knowledge and data properties and characteristics. These learned partitions will be used for constructing the indexing tree. Based on the optimized data partitioning, the patient similarity is refined 108. Node purity threshold checking 110 is performed to compare the initial patient similarity with the refined patient similarity to evaluate the optimized data partitioning. Other evaluation techniques are also contemplated, such as, e.g., retrieval precision. If node purity does not pass, optimized data partitioning 106 is repeated. If node purity does pass, an indexing tree is generated 112. The index tree may be used in a physician decision support system 114 to retrieve similar patients 118 from a query patient 116.

Figure 2:
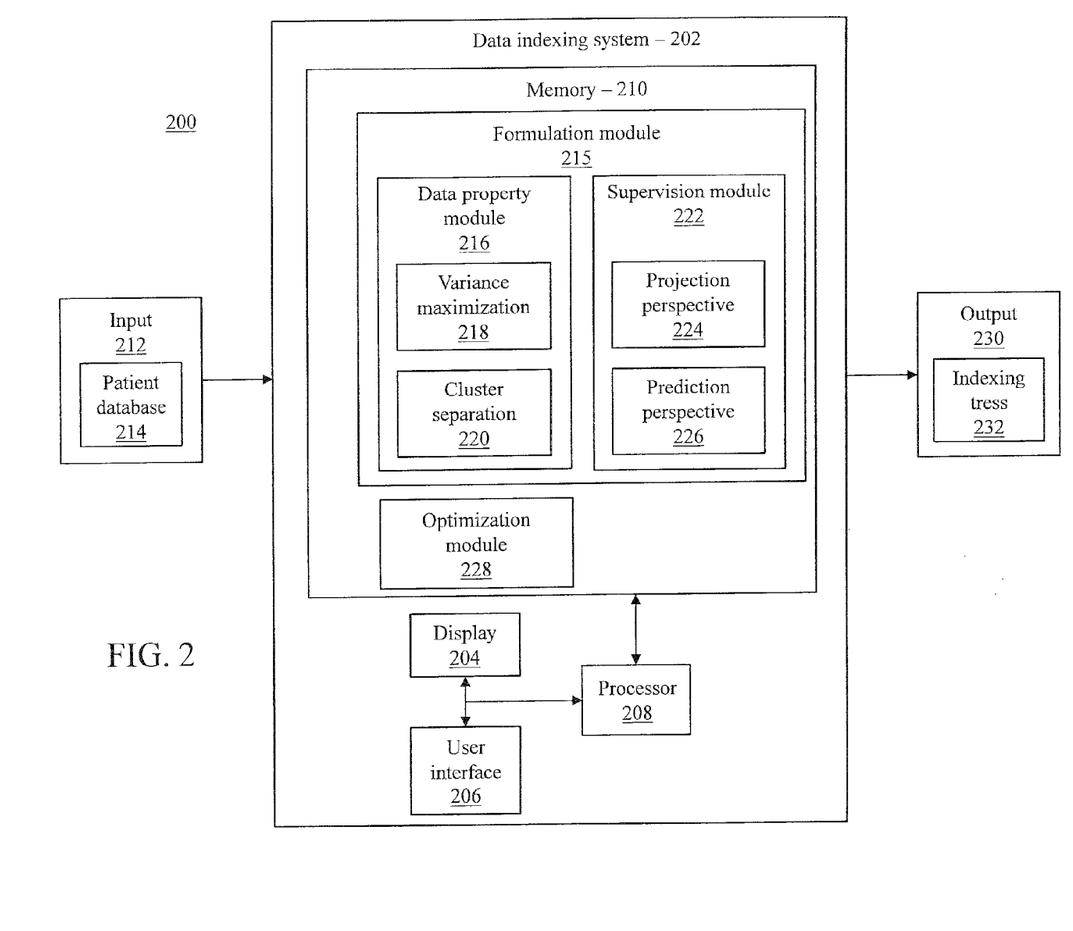
FIG. 2 is a block/flow diagram showing a system/method for data indexing in accordance with one illustrative embodiment.

Referring now to FIG. 2, a block/flow diagram of a system for data indexing 200 is illustratively depicted in accordance with one embodiment. A data indexing system may include a workstation or system 202. System 202 preferably includes one or more processors 208 and memory 210 for storing applications, modules, medical records and other data. The memory 210 may include a variety of computer readable media. Such media may include any media that is accessible by the system 202, and includes both volatile and non-volatile media, removable and non-removable media.

System 202 may include one or more displays 204 for viewing. The displays 204 may permit a user to interact with the system 202 and its components and functions. This may be further facilitated by a user interface 206, which may include a mouse, joystick, or any other peripheral or control to permit user interaction with the system 202 and/or its devices. It should be understood that the components and functions of the system 202 may be integrated into one or more systems or workstations.

System 202 may receive an input 212, which may include a patient database 214. Patient database 214 may include medical information for a set of patients and may be big data. For patient database 214, the set of patients is represented as $\chi = \{x_i\}_{i=1}^n$, where $x_i \in \mathbb{R}^d$ is the i-th data vector. $X \in \mathbb{R}^{d \times n}$ is used to represent the entire dataset, where the i-th column vector corresponds to the sample $x_i$. The goal is to build a tree structure to index the data points so that the nearest neighbors of a query vector q can be rapidly found. In medical scenarios, the data vectors in $\chi$ include patient profiles (e.g., EMRs) in the patient database and q is the profile of a query patient.

Patient database 214 preferably includes some pairwise supervision information on $\chi$ in terms of must- and cannot-links. For instance, if patient i and j are similar to each other, then a must-link is placed between $x_i$ and $x_j$. Similarly, if patient i and j are dissimilar to each other, a cannot-link is placed between them. A must-link set $\mathcal{M}$ is constructed by collecting all data pairs with must-links, and a cannot-link set C is constructed by collecting all data pairs with cannot-links. It is assumed that there are a total of l data points with pairwise labels represented as $X_l \in \mathbb{R}^{d \times l}$, where each data point in $X_l$ has at least one must- or cannot-link. Other forms of supervision information are also contemplated.

The data partitioning system 202 constructs binary space partitioning trees. From the root, the data points in $\chi$ are split into two halves by a partition hyperplane, and each half is assigned to one child node. Then each child node is recursively split in the same manner to create the tree.

Memory 210 may include formulation module 215 configured to formulate an objective function to index a dataset. At each node, the partition hyperplane w is determined by optimizing the objective of equation (1) as follows:

$$J(w) = J_S(w) + \lambda J_U(w) \quad (1)$$

where $J_S(w)$ is some supervised term involving expert knowledge and $J_U(w)$ is a pure data-dependent term without integrating any medical supervision. The supervision component $J_S(w)$ and the data property component $J_U(w)$ may be constructed using different implementations, according to user preferences or other factors. The objective of equation (1) may also include a constant $\lambda$ as a tradeoff parameter to balance the contributions from each term.

Formulation module 215 includes data property module 216 configured to construct the data property component $J_U(w)$ of the objective of equation (1) using all of the dataset (i.e., both supervised and unsupervised portions), but does not integrate the supervision information. Constructing $J_U(w)$ may include maximizing the data variance after projection or maximally separating the data clusters in its intrinsic space. The projection refers to the inner product of the data matrix X and the learned partition hyperplane w, which corresponds to the projected coordinates of X on the direction of w. Other implementations of maximizing the data variance are also contemplated.

Variance maximization 218 is configured to maximize the data variance after projection. The goal of this type of approach is to find the direction under which the variance of the projected data is maximized such that the binary partition of those directions will more likely produce a balanced tree. Therefore the constructed tree will not be as deep so that the nearest neighbors of a query data point can be quickly found.

In one embodiment, variance maximization 218 includes performing principal component analysis (PCA). PCA obtains the eigenvector from the data covariance matrix with the largest corresponding eigenvector. Suppose the data set has been centralized. $J_U(w)$ can be constructed as in equation (2):

$$J_{U_{PCA}}(w) = w^T X X^T w. \quad (2)$$

In another embodiment variance maximization 218 includes performing maximum variance unfolding (MVU). MVU maximizes the overall pairwise distances in the projected space by maximizing equation (3):

$$J_{U_{MVU}}(w) = \sum_{ij} (w^T x_i - w^T x_j)^2 \quad (3)$$
$$= w^T X(nI - ee^T) X^T w,$$

where I is the order n identify matrix, and e is the n-dimensional all-one vector.

$$I - \frac{1}{n} ee^T$$

is the data centralization matrix such that $$X\left(I - \frac{1}{n} ee^T\right) X^T$$

is equivalent to the data covariance matrix. Thus, the MVU of $J_U(w)$ and the PCA of $J_U(w)$ are the same up to a scaling factor. Other implementations of variance maximization 218 are also contemplated.

Cluster separation 220 is configured to maximally separate the data clusters in intrinsic space. Cluster separation 220 seek a projection direction under which the two balanced data clusters can be formed and equally distributed on the two sides of the median of the projected data. In other embodiments, data clusters may be distributed around other statistics measures, such as, e.g., the mean or weighted mean. Data clusters can be obtained by minimizing the following objective of equation (4):

$$\mathcal{J}_{U_{CS}}(w) = \sum_{x_i \in \mathcal{G}_1, x_i \in \mathcal{G}_2} w_{ij} = w^T X(D-W)X^T w \quad (4)$$

where $\mathcal{G}_1$ and $\mathcal{G}_2$ are the two data clusters. $W \in \mathbb{R}^{n \times n}$ is the data similarity matrix with its (i, j)-th entry computed as $$W_{ij} = \exp(-\alpha \|x_i - x_j\|^2). \quad (5)$$

$D \in \mathbb{R}^{n \times n}$ is a diagonal matrix with $D_{ii} = \Sigma_j W_{ij}$. One point to note is that $\mathcal{J}\mathcal{U}_{CS}(w)$ is minimized, instead of maximized. A potential bottleneck for constructing $\mathcal{J}\mathcal{U}_{CS}(w)$ is that an n×n data similarity matrix W is to be computed, as well as do matrix multiplication on X and D−W, which could be very time consuming when n is huge.

Formulation module 215 also includes supervision module 222 configured to construct the expert supervision term $\mathcal{J}_S(w)$ of the objective of equation (1) using the supervised portion of the data set. The construction of $\mathcal{J}_S(w)$ incorporates experts' supervision information on the data (i.e., leveraging the knowledge contained in $\mathcal{M}$ and C). Supervision module 222 may include projection perspective and prediction perspective. Other embodiments are also contemplated.

In one embodiment, the supervision term $\mathcal{J}_S(w)$ is constructed by projection perspective 224. Projection perspective 224 treats w as a pure projection that maps the data onto a one-dimensional space. After the projection, the goal is to have the data pairs in $\mathcal{M}$ be distributed as compact as possible, while the data pairs in C are distributed as scattered as possible. One straightforward criterion is to minimize the overall pairwise distances for the data pairs in $\mathcal{M}$ while maximizing the overall distances for the data pairs in C by minimizing the objective of equation (6).

$$\mathcal{J}_{S_{proj}} = \frac{1}{|\mathcal{M}|} \sum_{(x_i, x_j) \in \mathcal{M}} (w^T x_i - w^T x_j)^2 - \frac{1}{C} \sum_{(x_i, x_j) \in C} (w^T x_i - w^T x_j)^2 \quad (6)$$

$$= \sum_{ij} (w^T x_i - w^T x_j)^2 S_{proj_{ij}}$$

$$= w^T X_l (E-S) X_l^T w,$$

where S is an l×l matrix and its (i, j)-th entry is provided as $$S_{ij} = \begin{cases} \frac{1}{|\mathcal{M}|}, & \text{if } (x_i, x_j) \in \mathcal{M} \\ -\frac{1}{|C|}, & \text{if } (x_i, x_j) \in C \\ 0, & \text{otherwise} \end{cases} \quad (7)$$

and |·| denotes the cardinality of a set. E is an l×l diagonal matrix with $E_{ii} = \Sigma_j S_{ij}$.

In another embodiment, the expert supervision term $\mathcal{J}_S(w)$ is constructed by prediction perspective 226. Prediction perspective treats the projection as a linear prediction function f(x), such that the sign of f(x) indicates the class of x. If it is assumed that the data in each node are centralized, then the bias b in f(x) can be neglected such that $f(x) = w^T x$. The supervised term $\mathcal{J}_S$ under prediction perspective may be provided as follows:

$$\mathcal{J}_{S_{pred}} = \frac{1}{|\mathcal{M}|} \sum_{(x_i, x_j) \in \mathcal{M}} w^T x_i x_j^T w - \frac{1}{|C|} \sum_{(x_i, x_j) \in C} w^T x_i x_j^T w \quad (8)$$

$$= w^T \left( \frac{1}{|\mathcal{M}|} \sum_{(x_i, x_j) \in \mathcal{M}} x_i x_j^T - \frac{1}{|C|} \sum_{(x_i, x_j) \in C} x_i x_j^T \right) w$$

$$= w^T X_l S X_l^T w$$

where $S \in \mathbb{R}^{l \times l}$ is a symmetric matrix with its (i, j)-th entry provided as in equation (7).

Note that the above unsupervised components $\mathcal{J}\mathcal{U}_{PCA}$, $\mathcal{J}\mathcal{U}_{MVU}$ and supervised component $\mathcal{J}_{S_{pred}}$ apply maximization, while unsupervised component $\mathcal{J}\mathcal{U}_{CS}$ and supervised component $\mathcal{J}_{S_{proj}}$ apply minimization. To combine both components to form a semi-supervised scheme, the sign of the tradeoff parameter λ is adjusted to achieve consistence. For instance, if $\mathcal{J}\mathcal{U}_{PCA}$ is used as the data property component and $\mathcal{J}_{S_{pred}}$ as the supervision component, equation (1) can be rewritten as in equation (9):

$$\mathcal{J} = \mathcal{J}_{S_{pred}} + \mathcal{J}_{U_{PCA}} \quad (9)$$

$$= w^T (XSX^T + \lambda XX^T) w$$

$$= w^T A w,$$

where $A = XSX^T \lambda XX^T$ is a constant matrix absorbing both data property and supervision information. In this example, the coefficient λ is nonnegative.

Memory 210 also includes optimization module configured to optimize the objective of equation (1) based on the construction of the data property component $\mathcal{J}\mathcal{U}(w)$ and the supervision component $\mathcal{J}_{S_S}(w)$. No matter what the choices of $\mathcal{J}_{S_S}(w)$ and $\mathcal{J}\mathcal{U}(w)$ are, the final objective $\mathcal{J}$ can always be rewritten in the form of $\mathcal{J} = w^T A w$, as shown in one of the examples in equation (10). The matrix $A \in \mathbb{R}^{d \times d}$ is some matrix having different concrete forms depending on the specific choices of both supervised and unsupervised components.

$$\max_w w^T A w$$

$$\text{s.t. } w^T w = 1. \quad (10)$$

Equation (10) becomes a Rayleigh Quotient optimization problem, and the optimal solution w* can be obtained as the eigenvector of A whose corresponding eigenvalue is the largest (or smallest if a minimization problem is formed). Optimal partitioning is performed over the patient data for a given definition of patient similarity. Patient similarity may include any distance metric in the projected space, such as, e.g., the Euclidean distance. The similarity measure is different for each partition because of the different projections. Optimization is performed to recursively partition the patient database 214 until the sub-patient population becomes more homogenous (i.e., the projected patient vectors are more similar to each other), or the size of the population reaches a threshold value (e.g., 1 percent of the entire patient population). The optimization of the objective of equation (1) results in an indexing tree 232 of the patient database 214, which may be part of output 230.

The space and time complexities of the data partitioning system 202 have been analyzed. For space complexity, the data median for each node is stored for partitioning, which has O(n) space. Moreover, additional storage is utilized to store the projection for each node, resulting in a complexity of O(dn). Thus, the complete space complexity is O((d+1)n).

The computational cost of the data partitioning system 202 lies in the following aspects: 1) construction of the matrix A over the entire dataset; 2) extracting the projections by eigen-decomposition; and 3) computing the projected points. Here, the time cost for calculating $\jmath_S$ is omitted since it is assumed that l<<n for general semi-supervised settings. Specifically, it takes $O(nd^2)$ to compute the data covariance matrix (as in variance maximization 218) or $O(n^2d)$ to compute data similarity matrix (as in cluster separation 220). To decompose a matrix $\jmath$ with the size d×d to derive the principal projections, it takes $O(d^3)$. Finally, given the learned projection, it takes O(nd) to perform the multiplication to derive the one dimension projected points. Note that the above time complexity is estimated for the upper bound since as the recursive partition goes on, each node reduces exponentially.

Performance of the indexing approaches discussed above may be evaluated by node purity and retrieval precision. Other evaluation approaches are also contemplated.

Node purity measures the label consistency of the data points contained in individual tree nodes. Node purity may be expressed as in equation (11).

$$\text{Purity}(e) = \max_c |x_i \in e, l_i = c|/|e| \qquad (11)$$

where e is the set of data points in a node on the indexing tree and |e| is its cardinality. $|x_i \in e, l_i = c|$ indicates the number of data points in e with the same class label c. The computed node purity for leaf nodes is called leaf purity, which directly reflects the search accuracy.

For a given query data point x, its nearest neighbors can be found by traversing x over the tree from the root node to the leaf node. The retrieval precision for the query x is provided in equation (12).

$$\text{Precision}(x) = |x_i \in e(x), l_i = l(x)|/|e(x)| \qquad (12)$$

where e(x) is the set of nearest neighbors of x, which is obtained from the leaf node which x falls in. Let l(x) indicate the label of x. Then $|x_i \in e(x), l_i = l(x)|$ is the number of data points in e(x) with the same label as x.

Figure 3:
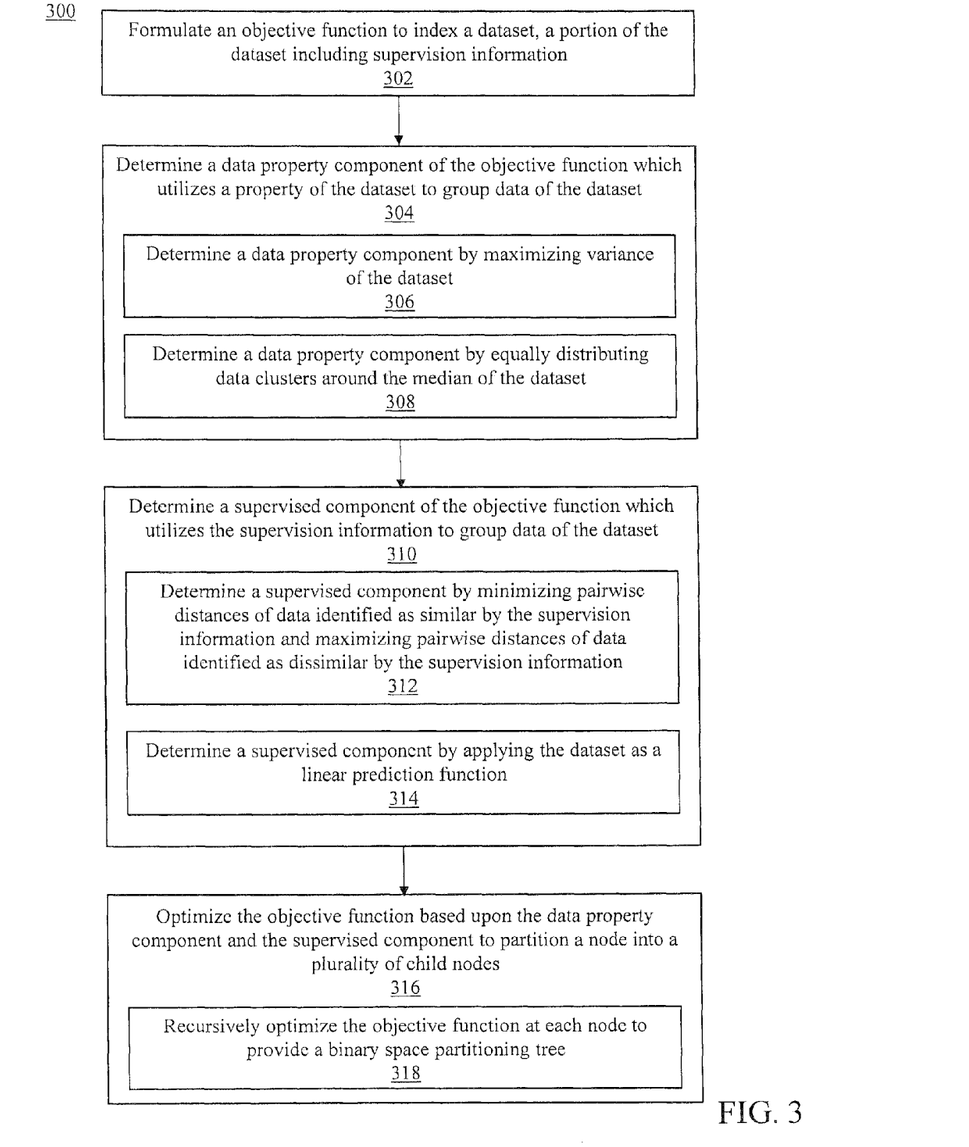
FIG. 3 is a block/flow diagram showing a system/method for data indexing in accordance with one illustrative embodiment.

Referring now to FIG. 3, a block/flow diagram showing a method for data indexing is illustratively depicted in accordance with one embodiment. In block 302, an objective function is formulated to index a dataset. The dataset may include patient medical information, such as, e.g., EMR. A portion of the dataset includes supervision information while the remaining portion does not include supervision information. Supervision information may include pairwise must-links and cannot-links. Must-links identify a pair of data (e.g., patient) that are similar to each other. Cannot-links identify a pair of data that are dissimilar to each other. The objective function includes a supervised component, which only use the supervised portion of the data along with their supervision information, and a data property component, which uses both supervised and unsupervised data. The objective function also includes a tradeoff parameter to balance the contributions of the supervised component and the data property component.

In block 304, a data property component of the objective function is determined. The data property component utilizes a property of the dataset to group data of the dataset. The data property component uses both supervised and unsupervised portions of the dataset, but does not integrate any of the supervision information. The data property component may be determined by maximizing the variance 306 or separating clusters 308. Other methods are also contemplated.

In one embodiment, in block 306, the data property component is determined by maximizing the variance of the dataset. The variance of the projected data is maximized such that the binary partition produces a balanced tree. Variance maximization may include applying Principal Component Analysis (PCA) to obtain the eigenvector from the data covariance matrix with the largest corresponding eigenvector. Variance maximization may also include applying maximum variance unfolding to maximize overall pairwise distances, which is mathematically equivalent to PCA. Other methods of variance maximization are also contemplated.

In another embodiment, in block 308, the data property component is determined by equally distributing data clusters around the median of the dataset. Other statistical measures may also be applied, such as, e.g., mean, weighted mean, etc. Clusters are separated such that two balanced data clusters are formed and equally distributed around the median of the projected data.

In block 310, a supervised component of the objective function is determined. The supervised component utilizes the supervision information to group data of the dataset.

In one embodiment, in block 312, the supervised component is determined by projection perspective. The goal of projection perspective is to distribute similar data pairs as compact as possible while distributing dissimilar data pairs as scattered as possible. Projection perspective includes minimizing pairwise distances of data identified as similar by the supervision information and maximizing pairwise distances of data identified as dissimilar by the supervision information.

In another embodiment, in block 314, the supervised component is determined by prediction perspective. The projections of patient vectors of the dataset can be viewed as linear predictions of their corresponding outcomes.

In block 316, the objective function is optimized based on the data property component and the supervised component to partition a node into a plurality of child nodes. Preferably, the plurality of child nodes is two child nodes. In block 318, the objective function is recursively optimized at each node to provide a binary space partitioning tree. Partitioning is recursively performed until the sub-patient population becomes more homogeneous or the size of the population reaches a threshold.

Having described preferred embodiments of a system and method for indexing of large scale patient set (which are intended to be illustrative and not limiting), it is noted that modifications and variations can be made by persons skilled in the art in light of the above teachings. It is therefore to be understood that changes may be made in the particular embodiments disclosed which are within the scope of the invention as outlined by the appended claims. Having thus described aspects of the invention, with the details and particularity required by the patent laws, what is claimed and desired protected by Letters Patent is set forth in the appended claims.

What is claimed is:

1. A non-transitory computer readable storage medium comprising a computer readable program for indexing data, wherein the computer readable program when executed on a computer causes the computer to perform the steps of:

formulating an objective function to index a dataset, a portion of the dataset including supervision information;

determining a data property component of the objective function which utilizes a property of the dataset to group data of the dataset, wherein determining the data property component includes maximizing a variance of the dataset, the maximizing the variance including applying maximum variance unfolding by forming a projection as an inner product of a data matrix and a learned partition hyperplane and maximizing overall pairwise distances in a projected space;

determining a supervised component of the objective function which utilizes the supervision information to group data of the dataset; and optimizing the objective function using a processor based upon the data property component and the supervised component to partition a node into a plurality of child nodes.

2. The system as recited in claim 1, wherein the variance maximization module is further configured to apply a principal component analysis.

3. The non-transitory computer readable storage medium as recited in claim 1, wherein optimizing the objective function includes recursively optimizing the objective function at each node to provide a binary space partitioning tree.

4. The non-transitory computer readable storage medium as recited in claim 1, wherein maximizing the variance further includes applying principal component analysis.

5. The non-transitory computer readable storage medium as recited in claim 1, wherein determining the data property component includes clustering data around a median of the dataset.

6. The non-transitory computer readable storage medium as recited in claim 1, wherein determining the supervised component includes minimizing pairwise distance of similar data identified by the supervision information and maximizing pairwise distance of dissimilar data identified by the supervision information.

7. The non-transitory computer readable storage medium as recited in claim 1, wherein determining the supervised component includes applying the dataset as a linear prediction function.

8. The non-transitory computer readable storage medium as recited in claim 1, wherein the objective function includes a tradeoff parameter to balance contributions from the data property component and the supervision component.

9. The non-transitory computer readable storage medium as recited in claim 1, wherein the supervision information includes must-links indicating pairs of data that are similar to each other and cannot-links indicating pairs of data that are dissimilar to each other.

10. The non-transitory computer readable storage medium as recited in claim 1, wherein the dataset includes patient medical information.

11. A system for indexing data, comprising:

a formulation module configured to formulate an objective function to index a dataset stored on a non-transitory computer readable storage medium, a portion of the dataset including supervision information;

a data property module configured to determine a data property component of the objective function which utilizes a property of the dataset to group data of the dataset, the data property module including a variance maximization module configured to maximize a variance of the dataset, the maximizing the variance including applying maximum variance unfolding by forming a projection as an inner product of a data matrix and a learned partition hyperplane and maximizing overall pairwise distances in a projected space;

a supervision module configured to determine a supervised component of the objective function which utilizes the supervision information to group data of the dataset; and an optimization module configured to optimize the objective function based upon the data property component and the supervised component to partition a node into a plurality of child nodes.

12. The system as recited in claim 11, wherein the optimization module is further configured to recursively optimize the objective function at each node to provide a binary space partitioning tree.

13. The system as recited in claim 11, wherein the data property module further comprises a cluster separation module configured to cluster data around a median of the dataset.

14. The system as recited in claim 11, wherein the supervision module further comprises a projection perspective module configured to minimize pairwise distance of similar data identified by the supervision information and maximize pairwise distance of dissimilar data identified by the supervision information.

15. The system as recited in claim 11, wherein the supervision module further comprises a prediction perspective module configured to apply the dataset as a linear prediction function.

16. The system as recited in claim 11, wherein the objective function includes a tradeoff parameter to balance contributions from the data property component and the supervision component.

17. The system as recited in claim 11, wherein the supervision information includes must-links indicating pairs of data that are similar to each other and cannot-links indicating pairs of data that are dissimilar to each other.

* * * * *